United States Patent
Hamaguchi et al.

(10) Patent No.: US 6,495,096 B1
(45) Date of Patent: Dec. 17, 2002

(54) DEODORANT AND PROCESS FOR DEODORIZATION USING SAID DEODORANT

(75) Inventors: Takayoshi Hamaguchi, Chiba-ken (JP); Kazuyuki Minato, Chiba-ken (JP); Toshimi Matsumoto, Ibaraki-ken (JP); Tadashi Shimomura, Chiba-ken (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 47 days.

(21) Appl. No.: 09/124,839

(22) Filed: Jul. 30, 1998

(51) Int. Cl.$^7$ .................................................. A61L 9/00
(52) U.S. Cl. .......................................... 422/5; 210/764
(58) Field of Search ................................ 422/5; 210/764

(56) References Cited

U.S. PATENT DOCUMENTS

| | | | |
|---|---|---|---|
| 3,966,450 A | * 6/1976 | O'Neill et al. | |
| 4,307,067 A | * 12/1981 | Tagawa et al. ................. | 422/5 |
| 4,681,687 A | * 7/1987 | Mouche et al. ............. | 210/764 |
| 4,917,820 A | * 4/1990 | Matsumoto et al. ......... | 252/397 |
| 5,336,431 A | * 8/1994 | Richards et al. ................ | 422/5 |
| 5,605,635 A | * 2/1997 | David ............................. | 422/5 |
| 5,792,342 A | * 8/1998 | Heller et al. ................ | 210/96.1 |
| 5,984,993 A | * 11/1999 | Mainz et al. .................... | 71/21 |

OTHER PUBLICATIONS

Van Nostrand's Scientific Encyclopedia, Sixth Edition, vol. 1, Van Nostrand Reinhold Company, Inc., 1983.*
The Condensed Chemical Dictionary, Tenth Edition, Van Nostrand Reinhold Company Inc., 1981.*

* cited by examiner

*Primary Examiner*—Krisanne Thornton
(74) *Attorney, Agent, or Firm*—Antonelli, Terry, Stout & Kraus, LLP

(57) ABSTRACT

A deodorant, for substances containing hydrogen sulfide or mercaptans, which includes a combination of a peroxide and a nitrate ion, a combination of a peroxide, a nitrate ion and a metal salt, or a combination of a chelating agent and one of the above combinations, and a process for deodorization comprising treating a substance for treatment, containing hydrogen sulfide or mercaptans, with the above deodorant. Smell caused by hydrogen sulfide or mercaptans is effectively removed by the deodorant. Smell from waste water, sludge, and water discharged from washing apparatuses can be efficiently removed with use of the deodorant in a small amount in accordance with this process.

33 Claims, 7 Drawing Sheets

TO A SEWAGE DISPOSAL PLANT

ABOUT 5km

TO A SEWAGE DISPOSAL PLANT

ABOUT 3km

DEODORANT AND PROCESS FOR DEODORIZATION USING SAID DEODORANT

BACKGROUND OF THE INVENTION

1. Field of the Invention

The present invention relates to a deodorant and a process for deodorization using said deodorant. More particularly, the present invention relates to a deodorant which can efficiently remove smell caused by hydrogen sulfide or mercaptans with use in a small amount and a process for deodorization which enables rapidly and efficiently removing smell caused by hydrogen sulfide or mercaptans in waste water, sludge formed in treatments of waste water, such as raw sludge, excess sludge, digested sludge, and flocculated sludge, water discharged from washing apparatuses, and mixtures of these substances with use of the above deodorant in a small amount.

2. Description of the Related Arts

Recent concentration of population to urban and suburban areas leads to consumption of a large amount of water. After being used in such areas, the water resources become waste water containing various organic and inorganic substances, which is discharged into public sewer systems or pits in buildings. In the process of treatment of waste water in sewage treatment plants, large amounts of raw sludge, excess sludge, and digested sludge are formed. In business plants, such as large manufacturing plants, regulations on waste water have been made stricter after occurrence of serious environmental pollution in rivers and seas, and treatments of waste water are enforced to achieve the specified quality of waster water. A large amount of sludge is formed in the precipitation treatment with flocculation or the treatment with active sludge in business plants.

Such waste water and sludge contain sulfates and large amounts of components causing buildup of BOD (biological oxygen demand). In waste water and sludge, sulfate reduction bacteria are generally present and conduct production activities, reducing sulfates in the sludge to hydrogen sulfide. The formed hydrogen sulfide is discharged into the gas phase because hydrogen sulfide is a gas at a room temperature. Hydrogen sulfide is toxic and has unpleasant smell. Leak of hydrogen sulfide from manholes of the sewer system or from underground of buildings causes the problem of smell to residents in the area. Moreover, there is the possibility of danger to workers during treatments of sludges. Hydrogen sulfide is oxidized by sulfate oxidization bacteria attached to facilities of concrete and the air and dissolved into mist to form sulfuric acid. Sulfuric acid thus formed corrodes concrete which is alkaline and metal to cause fatal defects to the structure of buildings. Mercaptans are formed in the process of putrefaction of waste water and sludge in a manner similar to the formation of hydrogen sulfide to cause the problem of smell.

To prevent generation of smell and corrosion of structures, pH may be adjusted to an alkaline condition using sodium hydroxide or the like to suppress vaporization of hydrogen sulfide. However, hydrogen sulfide itself is not decomposed or removed in accordance with this process. Hydrogen sulfide is generated again or alkali scales are formed when the treated water is neutralized. Therefore, this process is not satisfactory. As another process, hydrogen peroxide may be added to oxidize components causing smell. This process has a problem that, when hydrogen peroxide is used in a small amount, hydrogen sulfide is formed again from products of the oxidation, such as sulfur or sulfate ion, by the action of bacteria after sludge is left standing for a long time although hydrogen sulfide and mercaptans can be removed once. As another process, a metal salt may be added to fix hydrogen sulfide as a salt of the metal. In this process, hydrogen sulfide is fixed as a metal sulfide by the reaction of the metal ion and hydrogen sulfide, but this process has a problem that a large amount of sludge is formed.

Waste water or sludge may be treated with active charcoal to adsorb hydrogen sulfide. In this process, however, the used active charcoal must be regenerated or replaced with fresh active charcoal when the adsorption is saturated, and this causes economic disadvantage because replacing active charcoals requires an additional operation and the cost of regeneration is, high.

Alternatively, smell may be removed by passing waste water or sludge through a biological phase which is supported on a support and packed. However, this process has problems that a large apparatus is necessary and that maintenance and control of the biological phase is not easy. Generation of hydrogen sulfide may be suppressed by addition of a salt of nitric acid into waste water. However, the salt of nitric acid itself cannot oxidize sulfides.

SUMMARY OF THE INVENTION

Under the above circumstances, the first object of the present invention is to provide a deodorant which can efficiently remove smell caused by hydrogen sulfide or mercaptans with use in a small amount.

The second object of the present invention is to provide a process for deodorization which enables rapidly and efficiently removing smell caused by hydrogen sulfide or mercaptans in waste water, sludge formed in treatments of waste water, such as raw sludge, excess sludge, digested sludge, and flocculated sludge, water discharged from washing apparatuses, and mixtures of these substances with use of a deodorant in a small amount.

As the result of extensive studies by the present inventors to achieved the above objects, it was found that the first object can be achieved by a deodorant comprising a combination of a peroxide and a nitrate ion, a combination of a peroxide, a nitrate ion, and a metal salt, or a combination of a chelating agent and one of the above combinations. It was also found that the second object can be achieved by a process comprising treating a substance for treatment containing hydrogen sulfide or mercaptans with the above deodorant.

The present invention has been completed on the basis of the above knowledge.

Accordingly, the present invention provides:

(1) A deodorant for substances containing hydrogen sulfide and/or mercaptans which comprises a combination of a peroxide and a nitrate ion (referred to as deodorant 1, hereinafter);

(2) A deodorant for substances containing hydrogen sulfide and/or mercaptans which comprises a combination of a peroxide, a nitrate ion, and a metal salt (referred to as deodorant 2, hereinafter);

(3) A process for deodorization comprising treating a substance for treatment containing at least one compound selected from the group consisting of hydrogen sulfide and mercaptans with a deodorant described in (1) (referred to as process for deodorization 1, hereinafter); and (4) A process for deodorization comprising treating a substance for treatment containing at least one compound selected from the group consisting of hydrogen sulfide and mercaptans with a deodorant described in (2) (referred to as process for deodorization 2, hereinafter).

Figure 1:
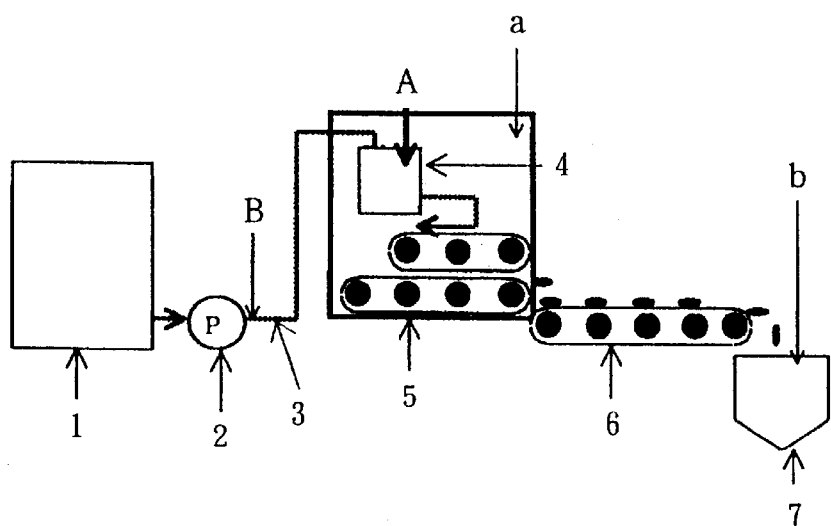
FIG. 1 shows a schematic diagram exhibiting the process for treating sludge conducted in Example 31.

Numbers and characters in the Figures have the following meanings:

1: A sludge tank
4: A tank for mixing with a flocculating agent
5: A dehydrator
6: A conveyor
7: A hopper for a dehydrated cake
11: A pumping station
12: A pit
14: A sewer pipe
31: A raw water tank
33: A screen
34: An adjustment tank
36: A mixing tank
38: A floating tank
A: A flocculating agent
D: Waste water flowing into the sewage disposal plant
F: Concentrated sludge

DESCRIPTION OF THE PREFERRED EMBODIMENTS

Deodorant 1 of the present invention comprises a combination of a peroxide and a nitrate ion, and deodorant 2 of the present invention comprises a combination of a peroxide, a nitrate ion, and a metal salt.

As the peroxide used in deodorant 1 and deodorant 2, for example, hydrogen peroxide, peracetic acid, salts of persulfuric acid, salts of percarbonic acid, salts of perboric acid, and other inorganic and organic peroxides can be used. Hydrogen peroxide and salts of percarbonic acid are preferable. The peroxide may be used singly or as a combination of two or more types.

Hydrogen peroxide is commercially available as a 35% by weight solution or a 60% by weight solution. A commercial hydrogen peroxide may be used directly or after dilution to facilitate mixing with a substance for treatment. As the salt of percarbonic acid, sodium percarbonate is preferable from the standpoint of the effect and the economy.

The nitrate ion in deodorant 1 and deodorant 2 can be supplied as nitric acid or a salt of nitric acid. Nitric acid is commercially available as a 68% by weight solution or a 62% by weight solution. A commercial nitric acid may be used directly or after dilution. Examples of the salt of nitric acid include inorganic salts of nitric acid, such as sodium nitrate, potassium nitrate, calcium nitrate, and ammonium nitrate. Anhydrated salts and hydrated salts can be used as the salt of nitric acid. The amount of the nitrate ion relative to the peroxide is not particularly limited and is generally about 2 to 200% by weight of the amount of the peroxide as 100% hydrogen peroxide.

Preferable examples of the metal salt used in deodorant 2 of the present invention include salts of metals belonging to Groups 6 to 12 and 14 of the Periodic Table. Examples of the metal include metals of Group 6, such as chromium, metals of Group 7, such as manganese, metals of Group 8, such as iron, metals of Group 9, such as cobalt, metals of Group 10, such as nickel, metals of Group 11, such as copper and silver, metals of Group 12, such as zinc, and metals of Group 14, such as tin and lead. Examples of the metal salt include inorganic salts, such as salts of sulfuric acid, salts of nitric acid, halides, and salts of perchloric acid, and organic salts, such as salts of oxalic acid and salts of formic acid. Hydroxides and oxides may also be used. Anhydrated salts and hydrated salts can be used as the metal salt. In the present invention, iron salts are preferably used from the standpoint of the effect and the economy. Examples of the iron salt include inorganic salts and organic salts described above and having an oxidation number of +2 or +3. Hydroxides and oxides can also be used, In general, an aqueous solution of an iron salt, such as a 37% aqueous solution of iron chloride, is used. Iron polysulfates may also be used as the iron salt. The above metal salt can be used singly or as a combination of two or more types.

When deodorants 1 and 2 of the present invention are used, the components of the deodorants may be added to a substance for treatment separately or as a mixture of the components prepared in advance. Alternatively, some of the components may be mixed to prepare a mixture, and the prepared mixture and the remaining components may be added to a substance for treatment.

In deodorants 1 and 2 of the present invention, it is preferable that a chelating agent is additionally used as the stabilizer when the peroxide and the nitrate ion or the peroxide, the nitrate ion, and the metal salts are mixed together in advance.

As the chelating agent, at least one compound selected from the group consisting of chelating agents having two or more carboxyl groups, salts of chelating agents having two or more carboxyl groups, chelating agents having two or more phosphono groups, and salts of chelating agents having two or more phosphono groups is used. Examples of the chelating agent having two or more carboxyl groups include ethylenediaminetetraacetic acid, nitrilotriacetic acid, diethylenetriaminepentaacetic acid, triethylenetetraminehexaacetic acid and polyhydroxycarboxylic acids.

Examples of the chelating agent having two or more phosphono groups include 1-hydroxyethylidene-1,1-diphosphonic acid, aminotri-(methylenephosphonic acid), ethylenediaminetetra(methylene-phosphonic acid), 1,2-propylenediaminetetra(methylenephosphonic acid), diethylenetriaminepenta(methylenephosphonic acid), hexamethylenediaminetetra(methylenephosphonic acid), triethylene-tetraminehexa (methylenephosphonic acid), triaminotriethylaminehexa-(methylenephosphonic acid), trans-1,2-cyclohexanediaminetetra-(methylenephosphonic acid), glycol ether diaminetetra(methylene-phosphonic acid), and tetraethylenehepta(methylenephosphonic acid).

The chelating agent may be used in the free form or in the form of a salt. When the chelating agent is used in the form of a salt, salts of alkali metals, salts of alkaline earth metals, ammonium salts, and salts of organic amines can be used. Sodium salts and ammonium salts are preferable. The amount of the chelating agent is preferably about 1 to 50,000 ppm by weight of the total amount of the peroxide and the nitrate ion although the amount depends on the amount of the nitrate ion. The amount of the chelating agent does not depend on the amount of the peroxide. Other stabilizers, such as phosphoric acid, may be used in combination, where necessary.

The processes for deodorization of the present invention are described in the following.

In the present invention, process for deodorization 1 comprises treating a substance for treatment containing hydrogen sulfide or mercaptans with deodorant 1 described above, i.e., with a peroxide and a nitrate ion. Process for deodorization 2 comprises treating a substance for treatment containing hydrogen sulfide or mercaptans with deodorant 2 described above, i.e., with a peroxide, a nitrate ion, and a metal salt.

The substance for treatment to which processes for deodorization 1 and 2 are applied is not particularly limited as long as at least one compound selected from the group consisting of hydrogen sulfide and mercaptans is contained. Examples of the substance for treatment include waste water, such as general waste water from households, waste water from manufacturing plants, and waste water discharged from washing apparatuses, and sludge, such as raw sludge, excess sludge, digested sludge, flocculated sludge, and mixtures of these sludges formed in the treatment of sewage, human sewage, and waste water from manufacturing plants.

In processes for deodorization 1 and 2 of the present invention, the amount of the peroxide as 100% by weight hydrogen peroxide is generally in the range of 1 to 2,000 mg/liter, preferably 2 to 1,000 mg/liter, of the substance for treatment. The amount of the nitrate ion is generally in the range of 1 to 2,000 mg/liter, preferably in the range of 2 to 1,000 mg/liter, of the substance for treatment. The order of addition of the peroxide and the nitrate ion is not particularly limited. These components may be added simultaneously or as a mixture prepared in advance. When the components are mixed in advance, a chelating agent may be added as the stabilizer, as described above.

In process for deodorization 2 of the present invention, the metal salt is additionally used. The metal salt is used in such an amount that the concentration by weight of the metal atom is generally 0.01 to 500 mg/liter, preferably 0.05 to 300 mg/liter, of the substance for treatment.

The order of the addition of the peroxide, the nitrate ion, and the metal salt is not particularly limited. The components may be added to the substance for treatment as a mixture prepared in advance. The components may be added separately at the same time or at different times. Alternatively, a mixture of two components may be prepared in advance, and the prepared mixture and the remaining component may be added at the same time or at different times. When the three components or the peroxide and the nitrate ion are mixed in advance, a chelating agent may be added as the stabilizer, as described above.

To conduct processes for deodorization 1 and 2 of the present invention efficiently, it is preferable that the peroxide and the nitrate ion or the peroxide, the nitrate ion, and the metal salts are added while being stirred so that the substance for treatment and the components of the deodorant are mixed well. As the method of stirring, any method, such as stirring in a mixing tank, stirring using mixing blades, and stirring using an in-line mixer, can be used as long as the components of the deodorant and the substance for treatment are mixed well.

As the method of addition of the components, any method can be used as long as the components are accurately supplied. For example, a constant delivery pump, such as a diaphragm pump and a plunger pump, may be used.

As a preferable example of the embodiment of process for deodorization 1 of the present invention, the peroxide and the nitrate ion are added into a pipe for transfer of waste water or sludge. Examples of the pipe for transfer of waste water or sludge include pipings for transfer of waste water from buildings to pits, pipings for transfer of waste water from pits to apparatuses for waste water treatment, pipings in pumping stations in sewage disposal apparatuses, pipings for transfer of sludge from tanks for concentration of sludge to sludge tanks in sewage disposal plants, and pipings for transfer of sludge from sludge tanks to dehydrators. However, the pipe for transfer of waste water is not limited to the above examples.

In the above embodiment, the amounts of the peroxide and the nitrate ion are the same as those described above. The peroxide and the nitrate ion may be added simultaneously or as a mixture prepared in advance. When the peroxide and the nitrate ion are added as a mixture prepared in advance, a chelating agent may be added as the stabilizer, as described above. A mixing apparatus, such as a static mixer, may be attached to a pipe for transfer of waste water or sludge to mix the peroxide and the nitrate ion and inject the obtained mixture into the pipe. As the method of addition of the components, any method can be used as long as the components are accurately supplied. For example, a constant delivery pump, such as a diaphragm pump and a plunger pump, may be used. The temperature of the treatment is not particularly limited. When the temperature is 10° C. or higher, advantageous reaction efficiency can be obtained.

As the preferable example of the embodiment of process for deodorization 2 of the present invention, (1) waste water or sludge may be treated with an iron salt and subsequently with a peroxide and a nitrate ion, or (2) waste water or sludge may be treated with an iron salt and a nitrate ion and subsequently with a peroxide.

In the process described in (1), waste water or sludge is first treated with an iron salt. After the treatment with the iron salt, the waste water or the sludge is treated with the peroxide and the nitrate ion. The peroxide and the nitrate ion may be added simultaneously or added as a mixture prepared in advance. When the peroxide and the nitrate ion are added as a mixture prepared in advance, a chelating agent may be added as the stabilizer, as described above. The mixture of the peroxide and the nitrate ion may be used directly after mixing or may be diluted so that the mixture can be easily mixed with the waste water or the sludge. The peroxide and the nitrate ion may also be added successively. When they are added successively, the order of the addition is not particularly limited.

In the process described in (2), waste water or sludge is first treated with an iron salt and a nitrate ion and subsequently with a peroxide. The iron salt and the nitrate ion may be added simultaneously or as a mixture prepared in advance. The mixture of the iron salt and the nitrate ion may be used directly after mixing or may be diluted so that the mixture can be easily mixed with the waste water or the sludge. The iron salt and the nitrate ion may also be added successively. When they are added successively, the order of the addition is not particularly limited.

In the processes described above, the amounts of the peroxide and the nitrate ion are the same as those described above. The iron salt is used in such an amount that the amount by weight of iron atom is generally 0.1 to 500 mg/liter, preferably 1 to 300 mg/liter, of the waste water or the sludge.

The deodorant of the present invention can effectively remove smell caused by hydrogen sulfide and mercaptans with use in a small amount. In accordance with the process for deodorization of the present invention, smell caused by hydrogen sulfide or mercaptans in waste water, sludge which is formed in treatments of waste water, such as raw sludge, excess sludge, digested sludge, and flocculated sludge, water discharged from washing apparatuses, and mixtures of these substances is removed rapidly and efficiently with use of the above deodorant in a small amount.

EXAMPLES

The present invention is described more specifically with reference to examples in the following. However, the present invention is not limited by the examples.

Example 1

To 100 ml of waste water which was taken from a pit in a building, contained 20 mg/liter of hydrogen sulfide, and had a pH of 6.8, a 7% by weight aqueous solution of hydrogen peroxide was added in such an amount that the concentration as 100% hydrogen peroxide in the waste water was 30 mg/liter (42.9 mg; 1.5 times as much as the amount by mol of hydrogen sulfide). Then, 2.74 mg of sodium nitrate was added so that the concentration of the nitrate ion was adjusted to 20 mg/liter. The change in the concentration of hydrogen sulfide with time in the liquid phase was measured in accordance with the colorimetric method using a lead acetate testing paper. The results are shown in Table 1.

Example 2

The same treatment as that conducted in Example 1 was conducted except that 2.4 mg of iron(III) chloride hexahydrate was added as the metal salt so that the concentration of the iron(III) ion was adjusted to 5 mg/liter. The results are shown in Table 1.

Example 3

The same treatment as that conducted in Example 1 was conducted except that 2.6 mg of manganese nitrate hexahydrate was added as the metal salt so that the concentration of the manganese(II) ion was adjusted to 5 mg/liter. The results are shown in Table 1.

Example 4

The same treatment as that conducted in Example 1 was conducted except that 2.0 mg of copper sulfate pentahydrate was added as the metal salt so that the concentration of the copper ion was adjusted to 5 mg/liter. The results are shown in Table 1.

Example 5

The same treatment as that conducted in Example 1 was conducted except that 1.0 mg of zinc chloride was added as the metal salt so that the concentration of the zinc ion was adjusted to 5 mg/liter. The results are shown in Table 1.

Example 6

The same treatment as that conducted in Example 1 was conducted except that 0.8 mg of silver nitrate was added as the metal salt so that the concentration of the silver ion was adjusted to 5 mg/liter. The results are shown in Table 1.

Example 7

The same treatment as that conducted in Example 1 was conducted except that 3.9 mg of chromium nitrate nonahydrate was added as the metal salt so that the concentration of the chromium ion was adjusted to 5 mg/liter. The results are shown in Table 1.

Example 8

The same treatment as that conducted in Example 1 was conducted except that 2.0 mg of cobalt chloride hexahydrate was added as the metal salt so that the concentration of the cobalt ion was adjusted to 5 mg/liter. The results are shown in Table 1.

Example 9

The same treatment as that conducted in Example 1 was conducted except that 2.5 mg of nickel nitrate hexahydrate was added as the metal salt so that the concentration of the nickel ion was adjusted to 5 mg/liter. The results are shown in Table 1.

Example 10

The same treatment as that conducted in Example 1 was conducted except that 1.5 mg of tin chloride pentahydrate was added as the metal salt so that the concentration of the tin ion was adjusted to 5 mg/liter. The results are shown in Table 1.

Example 11

The same treatment as that conducted in Example 1 was conducted except that 0.9 mg of lead triacetate trihydrate was added as the metal salt so that the concentration of the lead ion was adjusted to 5 mg/liter. The results are shown in Table 1.

Example 12

The same treatment as that conducted in Example 1 was conducted except that 1.8 mg of iron(II) chloride tetrahydrate was added as the metal salt so that the concentration of the iron(II) ion was adjusted to 5 mg/liter. The results are shown in Table 1.

Comparative Example 1

The same treatment as that conducted in Example 1 was conducted except that neither hydrogen peroxide nor a metal salt was added. The results are shown in Table 1.

TABLE 1

| | content of hydrogen sulfide in waste water (mg/liter) | | | |
|---|---|---|---|---|
| time (min) | 1 | 5 | 60 | 480 |
| Example 1 | 4 | 1 | 0 | 0 |
| Example 2 | 3 | 0 | 0 | 0 |
| Example 3 | 3 | 0 | 0 | 0 |
| Example 4 | 0 | 0 | 0 | 0 |
| Example 5 | 3 | 0 | 0 | 0 |
| Example 6 | 1 | 0 | 0 | 0 |
| Example 7 | 3 | 0 | 0 | 0 |
| Example 8 | 2 | 0 | 0 | 0 |
| Example 9 | 3 | 0 | 0 | 0 |
| Example 10 | 3 | 0 | 0 | 0 |
| Example 11 | 3 | 0 | 0 | 0 |
| Example 12 | 3 | 0 | 0 | 0 |
| Comparative Example 1 | 20 | 21 | 28 | 30 |

Example 13

To 200 ml of sewage sludge containing raw sludge and excess sludge, hydrogen peroxide was added in such an amount that the concentration in the sludge was 100 mg/liter as 100% hydrogen peroxide, and 16.3 mg of potassium nitrate was added so that the concentration of the nitrate ion was adjusted to 100 mg/liter. The sludge, hydrogen peroxide, and potassium nitrate were mixed together. The amounts of hydrogen sulfide and methyl mercaptan in the obtained mixture were measured in accordance with the head space method after the mixture was stirred for 5 minutes and after the mixture was left standing for 4 hours. The results are shown in Table 2.

Example 14

The same treatment as that conducted in Example 13 was conducted except that the amount of potassium nitrate was decreased to 8.1 mg so that the concentration of the nitrate ion was adjusted to 50 mg/liter, and zinc chloride was added in such an amount that the concentration of zinc was adjusted to 25 mg/liter. The results are shown in Table 2.

Comparative Example 2

The same treatment as that conducted in Example 13 was conducted except that neither zinc chloride nor potassium nitrate was added, but hydrogen peroxide alone was added in such an amount that the concentration was adjusted to 200 mg/liter. The results are shown in Table 2.

TABLE 2

| | hydrogen sulfide (ppm) | | methyl mercaptan (ppm) | |
|---|---|---|---|---|
| time | 5 min | 4 hr | 5 min | 4 hr |
| Example 13 | 0 | 1 | 1 | 2 |
| Example 14 | 0 | 0 | 1 | 1 |
| Comparative Example 2 | 0 | 100 | 4 | 7 |

When hydrogen peroxide alone was used for removal of hydrogen sulfide, a rapid effect was shown, but hydrogen sulfide was regenerated after the mixture was left standing for 4 hours. The sustained removal of hydrogen sulfide and methyl mercaptan was achieved by the additional use of potassium nitrate. The sustained removal could be achieved even at a decreased amount of potassium nitrate when zinc chloride is additionally used.

Example 15

A sludge produced by treatment of waste water discharged from a manufacturing plant was treated for deodorization in the following manner: a 7% by weight hydrogen peroxide was added in such an amount that the concentration was 150 mg/liter as 100% hydrogen peroxide; the obtained mixture was stirred for 1 minute; then, nitric acid was added in such an amount that the concentration of the nitrate ion was 30 mg/liter; the obtained mixture was stirred for 1 minute; and a 20% by weight solution of zinc chloride was added in such an amount that the concentration of zinc was 15 mg/liter. The amount of hydrogen sulfide in the obtained mixture was measured in accordance with the head space method after the mixture was stirred for 5 minutes and after the mixture was left standing for 4 hours. The results are shown in Table 3.

Example 16

The same treatment as that conducted in Example 15 was conducted except that the components of the deodorant were added in the following order: a 20% by weight solution of zinc chloride, a 7% by weight solution of hydrogen peroxide, and then nitric acid. The results are shown in Table 3.

Example 17

The same treatment as that conducted in Example 15 was conducted except that a 7% by weight solution of hydrogen peroxide, nitric acid, and a 20% by weight solution of zinc chloride were added simultaneously. The results are shown in Table 3.

TABLE 3

| | hydrogen sulfide (ppm) | |
|---|---|---|
| time | 5 min | 4 hr |
| Example 15 | 0 | 0 |
| Example 16 | 0 | 0 |
| Example 17 | 0 | 0 |

As shown above, difference in the order of addition of the peroxide, the nitrate ion, and the metal salt did not make any difference in the effect.

Example 18

To 1,000 ml of sludge produced by treatment of waste water discharged from a manufacturing plant, 0.34 g (corresponding to about 100 mg/liter of hydrogen peroxide and about 100 mg/liter of the nitrate ion) of a deodorant having a composition comprising 100.0 g of a 60% by weight hydrogen peroxide, 101.7 g of a 62% by weight nitric acid, and 0.2 g of a 25% by weight aqueous solution of diethylenetriaminepenta-(methylenephosphonic acid) was added, and the mixture was stirred. The amounts of hydrogen sulfide and methyl mercaptan in the obtained mixture were measured in accordance with the head space method using a gas detector after the mixture was stirred for 30 minutes and after the mixture was left standing for 24 hours and for 48 hours. The results are shown in Table 4. The deodorant showed a stability of 98% after being dipped into a hot water bath at 100° C. for 5 hours.

The stability was obtained in accordance with the following equation:

$$\text{stability} = \frac{\text{(concentration of hydrogen peroxide after heat treatment)}}{\text{(concentration of hydrogen peroxide before heat treatment)}} \times 100$$

Comparative Example 3

The same treatment was conducted as that conducted in Example 18 except that 0.50 g of a 60% by weight hydrogen peroxide (corresponding to 300 mg/liter of hydrogen peroxide) was added. The results are shown in Table 4.

The deodorant of the present invention used in Example 18 could exhibit the effect of deodorization for a longer time with use in a smaller amount than the deodorant used in Comparative Example 3.

TABLE 4

|  | hydrogen sulfide (ppm) | | | methyl mercaptan (ppm) | | |
|---|---|---|---|---|---|---|
| time (hr) | 0.5 | 24 | 48 | 0.5 | 24 | 48 |
| Example 18 | 0 | 0 | 0 | 5 | 2 | 2 |
| Comparative Example 3 | 0 | 120 | 400 | 5 | 2 | 2 |

Example 19

The same treatment as that conducted in Example 18 was conducted except that 0.42 g (corresponding to about 100 mg/liter of hydrogen peroxide and about 100 mg/liter of the nitrate ion) of a deodorant having a composition comprising 114.2 g of a 35% by weight hydrogen peroxide, 54.8 g of sodium nitrate, and 0.114 g of 1-hydroxyethylidene-1,1-diphosphonic acid to 1,000 ml of sludge of sewage. The results are shown in Table 5. The deodorant showed a stability of 100% after being dipped into a hot water bath at 100° C. for 5 hours.

Comparative Example 4

The same treatment as that conducted in Example 19 was conducted except that 0.55 g (corresponding to 400 mg/liter of the nitrate ion) of sodium nitrate was added. The results are shown in Table 5.

TABLE 5

|  | hydrogen sulfide (ppm) | | | | methyl mercaptan (ppm) | | | |
|---|---|---|---|---|---|---|---|---|
| time (hr) | 0.5 | 24 | 48 | 72 | 0.5 | 24 | 48 | 72 |
| Example 19 | 0 | 0 | 0 | 0 | 0 | 0 | 0 | 0 |
| Comparative Example 4 | 480 | 500 | 480 | 480 | 40 | 43 | 50 | 50 |

Example 20

To 500 ml of waste water which was discharged from a building and contained a large amount of suspended solids, 0.019 g (corresponding to about 10 mg/liter of hydrogen peroxide and about 6 mg/liter of the nitrate ion) of a deodorant having a composition comprising 100.0 g of a 35% by weight hydrogen peroxide, 34.4 g of a 62% by weight nitric acid, and 0.15 g of 1,2-propylenediaminetetra(methylenephosphonic acid) was added. After being stirred and mixed, the obtained mixture was dipped into a thermostatted vessel at 20° C. The amount of hydrogen sulfide in the liquid phase was measured after the mixture was dipped for 30 minutes, 12 hours, and 24 hours. The results are shown in Table 6. It was shown that, in accordance with the process of the present invention, generation of hydrogen sulfide could be suppressed completely even after 24 hours.

Comparative Example 5

The same treatment as that conducted in Example 20 was conducted except that no deodorant was added. The results are shown in Table 6.

Comparative Example 6

The same treatment as that conducted in Example 20 was conducted except that 0.028 g (corresponding to 20 mg/liter of hydrogen peroxide) of a 35% by weight hydrogen peroxide was added. The results are shown in Table 6.

TABLE 6

|  | hydrogen sulfide (ppm) | | |
|---|---|---|---|
| time (hr) | 0.5 | 12 | 24 |
| Example 20 | 0 | 0 | 0 |
| Comparative Example 5 | 4 | 5 | 12 |
| Comparative Example 6 | 0 | 0.5 | 3 |

Example 21

The same treatment as that conducted in Example 20 was conducted except that 0.018 g (corresponding to about 10 mg/liter of hydrogen peroxide and about 5 mg/liter of the nitrate ion) of a deodorant having a composition comprising 114.2 g of a 35% by weight hydrogen peroxide, 27.4g of sodium nitrate, and 0.114 g of 1-hydroxyethylidene-1,1-diphosphonic acid was added to 500 ml of sewage containing a large amount of suspended solids. The results are shown in Table 7.

Comparative Example 7

The same treatment as that conducted in Example 21 was conducted except that no deodorant was added. The results are shown in Table 7.

Comparative Example 8

The same treatment as that conducted in Example 20 was conducted except that 0.028 g of a 35% by weight hydrogen peroxide (corresponding to 20 mg/liter of hydrogen peroxide) was added. The results are shown in Table 7.

TABLE 7

|  | hydrogen sulfide (ppm) | | |
|---|---|---|---|
| time (hr) | 0.5 | 12 | 24 |
| Example 21 | 0 | 0 | 0 |
| Comparative Example 7 | 6 | 8 | 14 |

TABLE 7-continued

| | hydrogen sulfide (ppm) | | |
|---|---|---|---|
| time (hr) | 0.5 | 12 | 24 |
| Comparative Example 8 | 0 | 1 | 4 |

Example 22

The concentration of hydrogen peroxide in a deodorant having a composition comprising 100 g of a 35% by weight hydrogen peroxide, 28.7 g of nitric acid, and 0.01 g of a 25% by weight aqueous solution of diethylenetriaminepenta(methylenephosphonic acid) was measured after the deodorant was dipped into a hot water bath at 100° C. for 5 hours to obtain the stability. The result is shown in Table 8.

Example 23

The same treatment as that conducted in Example 22 was conducted except that 0.02 g of a 25% by weight aqueous solution of diethylenetriaminepenta(methylenephosphonic acid) was used. The result is shown in Table 8.

Example 24

The same treatment as that conducted in Example 22 was conducted except that no chelating agent was used. The result is shown in Table 8.

TABLE 8

| | stability (%) |
|---|---|
| Example 22 | 95.0 |
| Example 23 | 96.2 |
| Example 24 | 63.3 |

Example 25

The concentration of hydrogen peroxide in a deodorant having a composition comprising 100 g of a 35% by weight hydrogen peroxide, 42.8 g of potassium nitrate, and 0.005 g of 1,2-propylenediaminetetra-(methylenephosphonic acid) was measured after the deodorant was dipped into a hot water bath at 100° C. for 5 hours to obtain the stability. The result is shown in Table 9.

Example 26

The same treatment as that conducted in Example 25 was conducted except that 0.01 g of 1,2-propylenediaminetetra (methylene-phosphonic acid) was used. The result is shown in Table 9.

Example 27

The same treatment as that conducted in Example 25 was conducted except that no chelating agent was used. The result is shown in Table 9.

TABLE 9

| | stability (%) |
|---|---|
| Example 25 | 97.4 |
| Example 26 | 99.8 |
| Example 27 | 92.3 |

Example 28

The concentration of hydrogen peroxide in a deodorant having a composition comprising 100 g of a 35% by weight hydrogen peroxide, 38.4 g of sodium nitrate, and 0.01 g of a 25% by weight aqueous solution of diethylenetriaminepenta(methylenephosphonic acid) as the chelating agent was measured after the deodorant was left standing at a room temperature for 6 months to obtain the stability. The result is shown in Table 10.

Example 29

The same treatment as that conducted in Example 28 was conducted except that diethylenetriaminepentaacetic acid was used as the chelating agent. The result is shown in Table 10.

Example 30

The same treatment as that conducted in Example 28 was conducted except that no chelating agent was used. The result is shown in Table 10.

TABLE 10

| | stability (%) |
|---|---|
| Example 28 | 99.5 |
| Example 29 | 99.0 |
| Example 30 | 94.1 |

Example 31

FIG. 1 shows a schematic diagram exhibiting the process for treating sludge conducted in this Example. Sludge in a sludge tank 1 was transferred to a tank for mixing with a flocculating agent 4 through a transfer pipe 3 by a transfer pump 2, and a flocculating agent A was added to the sludge in the tank for mixing with a flocculating agent 4. The sludge was then dehydrated by a dehydrator 5, and the obtained dehydrated cake was transferred to a hopper for a dehydrated cake 7 by a conveyor 6.

Figure 4:
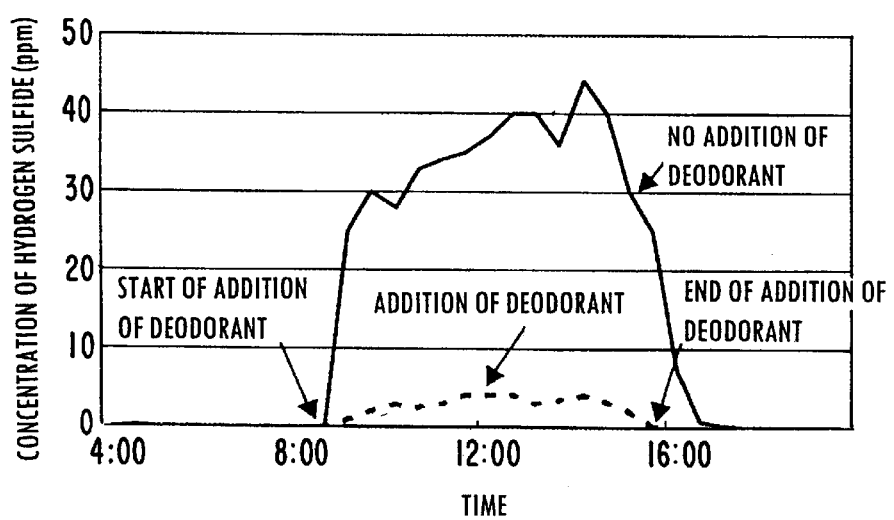
FIGS. 4 and 5 show graphs exhibiting the results obtained in Example 31.
Figure 5:
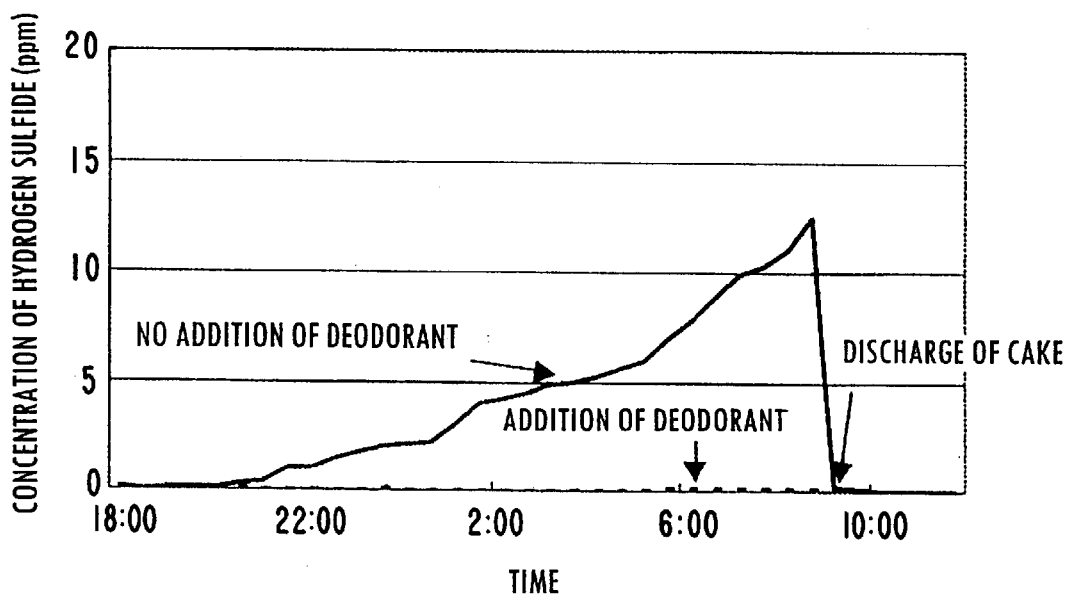

In the above process for treating sludge, a mixed solution B containing hydrogen peroxide and sodium nitrate was continuously added into the transfer pipe 3 immediately after the transfer pump 2 in such an amount that the concentration of hydrogen peroxide was 100 mg/liter as 100% hydrogen peroxide and the concentration of the nitrate ion was 100 mg/liter. The results of the measurement of the amounts of hydrogen sulfide and methyl mercaptan in the area around the dehydrator 5 (point of measurement of smell a) are shown in FIG. 4 and Table 11. The result of the measurement of the amount of hydrogen sulfide in the hopper for a dehydrated cake 7 (point of measurement of smell b) is shown in FIG. 5. Because the deodorant was added into the outlet of the transfer pump 2, the sludge and the deodorant were sufficiently mixed together, and the concentrations of hydrogen sulfide and methyl mercaptan in the area around the dehydrator and in the hopper for a dehydrated cake remarkably decreased.

TABLE 11

| | concentration of mercaptan (ppm) |
|---|---|
| No deodorant added | 6 |
| Deodorant added | N.D. |

Example 32

Figure 2:
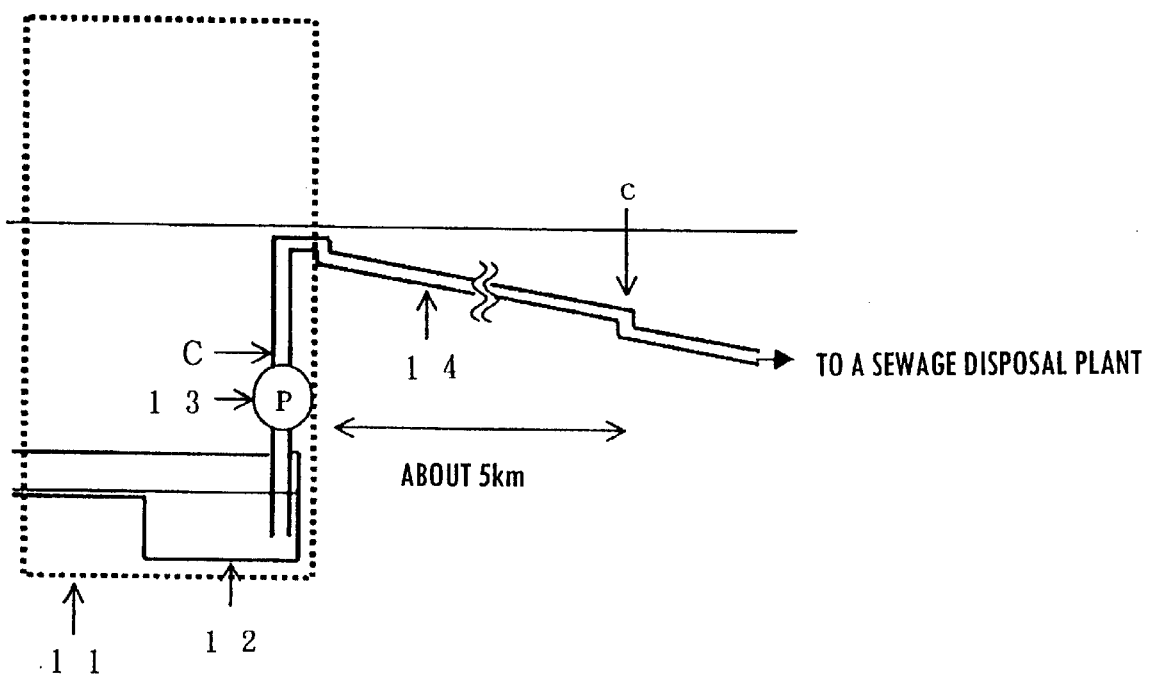
FIG. 2 shows a schematic diagram exhibiting the process for treating sewage conducted in Example 32.

FIG. 2 shows a schematic diagram exhibiting the process for treating sewage conducted in this Example. Sewage in a pit 12 of a pumping station 11 was transferred to a sewage disposal plant through a sewer pipe 14 by a transfer pump 13.

Figure 6:
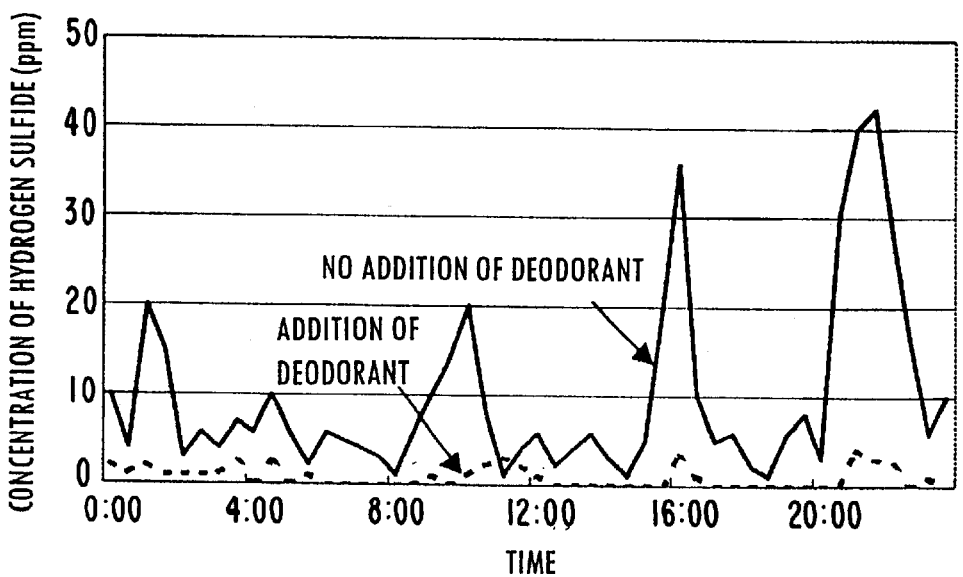
FIGS. 6 and 7 show graphs exhibiting the results obtained in Examples 32 and 33, respectively.

In the above process for treating sewage, a mixed solution C containing hydrogen peroxide and nitric acid was continuously added into an outlet of the transfer pump 13 in a pumping station 11 in such an amount that the concentration of hydrogen peroxide was 10 mg/liter as 100% hydrogen peroxide and the concentration of the nitrate ion was 5 mg/liter in the sewage. The result of the measurement of the concentration of hydrogen sulfide in a manhole (point of measurement of smell c) is shown in FIG. 6. By addition of the mixed solution containing hydrogen peroxide and the nitrate ion to the sewage, the formation of hydrogen sulfide could be suppressed in the manhole about 5 km downstream of the point of the addition.

Example 33

Figure 3:
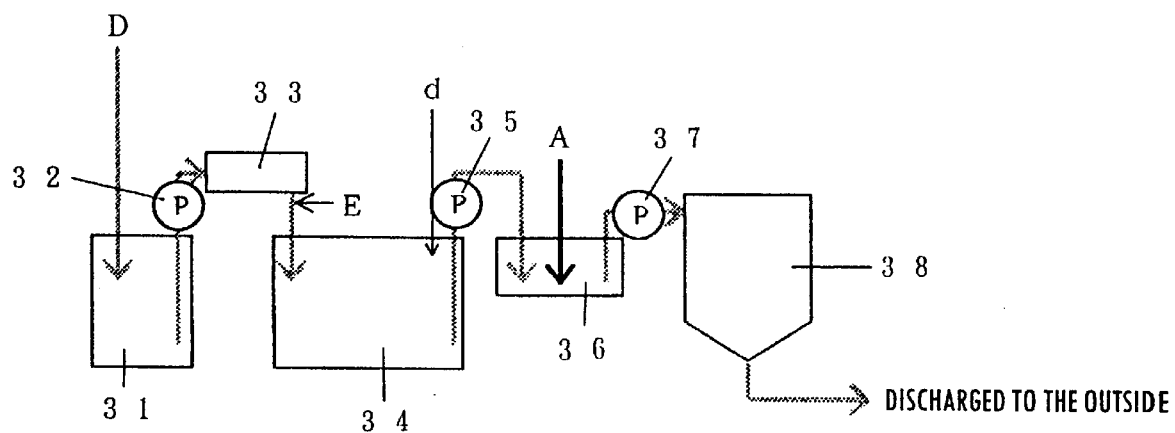
FIG. 3 shows a schematic diagram exhibiting the process for treating waste water conducted in Example 33.

FIG. 3 shows a schematic diagram exhibiting the process for treating waste water conducted in this Example. Waste water D which had flowed into a raw water tank 31 was transferred to an adjustment tank 34 through a screen 33 by a pump 32 and then to a mixing tank 36 by a pump 35. After a flocculating agent A was added to the waste water in the mixing tank 36, the waste water was transferred to a floatation tank 38 by a pump 37, and then discharged to the outside.

Figure 7:
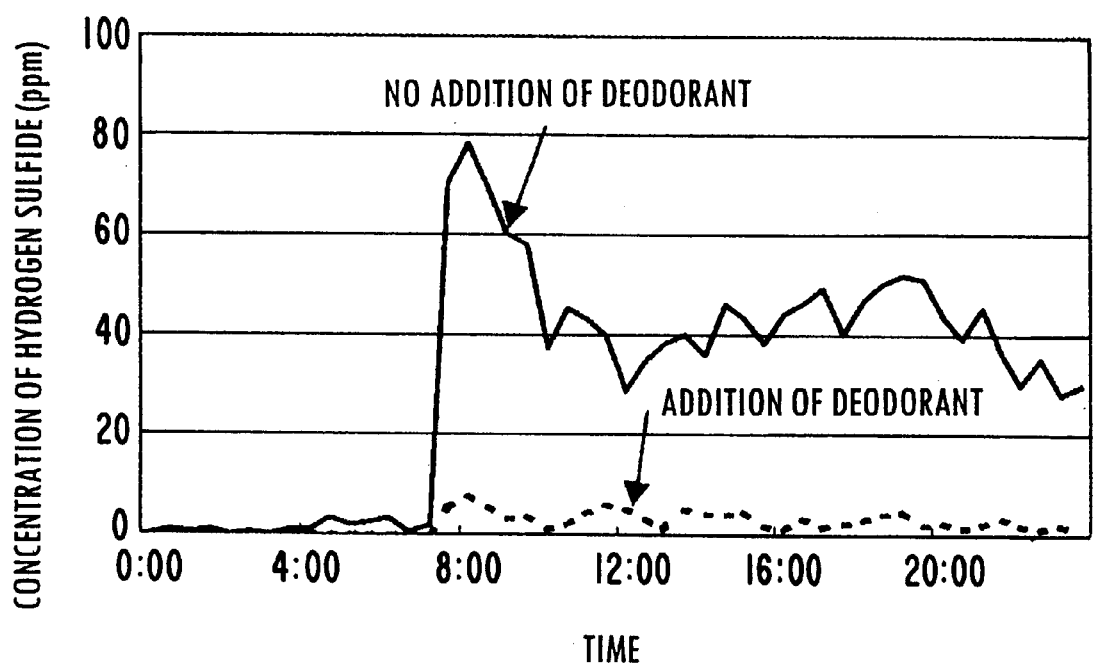

In the above process for treating waste water, a mixed solution E containing hydrogen peroxide and sodium nitrate was continuously added into an outlet of the pump 32 which transferred waste water D from the raw water tank 31 to the adjustment tank 34 in such an amount that the concentration of hydrogen peroxide was 30 mg/liter as 100% hydrogen peroxide and the concentration of the nitrate ion was 10 mg/liter in the waste water. The result of the measurement of hydrogen sulfide in the adjustment tank 34 (point of measurement of smell d) is shown in FIG. 7. By the addition of hydrogen peroxide and the nitrate ion, the concentration of hydrogen sulfide in the adjustment tank remarkably decreased, and smell of hydrogen sulfide around the apparatus for waste water treatment also decreased remarkably.

Example 34

Figure 8:
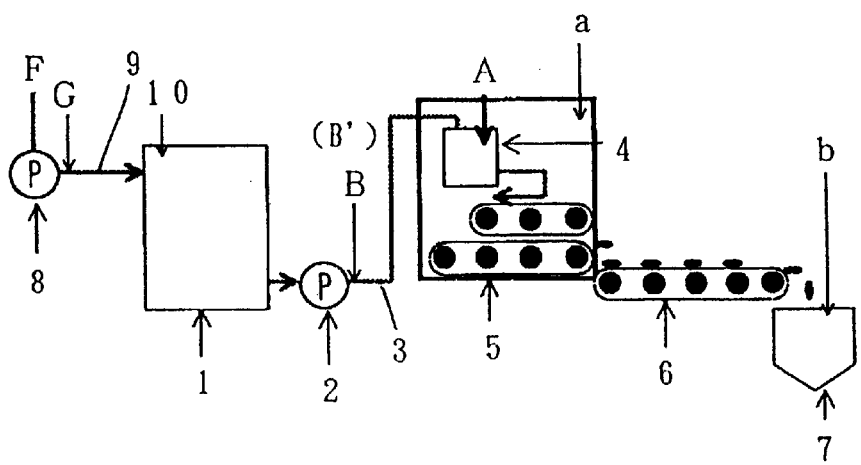
FIG. 8 shows a schematic diagram exhibiting the process for treating sludge conducted in Examples 34 to 36 and Comparative Examples 9 and 10.

FIG. 8 shows a schematic diagram exhibiting the process for treating sludge conducted in this Example and in Examples 35 and 36 and Comparative Examples 9 and 10 which are described below. Concentrated sludge F was transferred to a sludge tank 1 by a transfer pump 8. The sludge transferred to the sludge tank 1 was then transferred to a tank for mixing with a flocculating agent 4 through a transfer pipe 3 by a transfer pump 2, and a flocculating agent A was added to the sludge in the tank 4. After the treated sludge was dehydrated by a dehydrator 5, the obtained dehydrated cake is transferred to a hopper for a dehydrated cake 7 by a conveyor 6.

In the above process for treating sludge, polyferric sulfate was added into a transfer pipe 9 immediately after the transfer pump 8 in such an amount that the concentration in the sludge was 546 mg/liter (about 60 mg/liter as the iron atom), and a solution B prepared by mixing hydrogen peroxide and sodium nitrate in advance was continuously added into a transfer pipe 3 immediately after the transfer pump 2 which transferred the sludge from the sludge tank 1 in such an amount that the concentration of hydrogen peroxide was 100 mg/liter as 100% hydrogen peroxide and the concentration of the nitrate ion was 100 mg/liter in the sludge. The results of the measurement of hydrogen sulfide and methyl mercaptan in the dehydrator 5 (point of measurement of smell a) and in the hopper for a dehydrated cake 7 (point of measurement of smell b) are shown in Tables 12 and 13.

Comparative Example 9

The same treatment as that conducted in Example 34 was conducted except that neither polyferric sulfate, hydrogen peroxide, nor sodium nitrate was used. The results are shown in Tables 12 and 13.

Example 35

The same treatment as that conducted in Example 34 was conducted except that polyferric sulfate was not used. The results are shown in Tables 12 and 13.

TABLE 12

| | Example 34 | Example 35 | Comparative Example 9 |
|---|---|---|---|
| area around the dehydrator | | | |
| hydrogen sulfide (ppm) | 2 | 15 | 150 |
| methyl mercaptan (ppm) | N.D. | N.D. | 8 |

TABLE 13

| | Example 34 | Example 35 | Comparative Example 9 |
|---|---|---|---|
| inside the hopper for dehydrated cake | | | |
| hydrogen sulfide (ppm) | 0.1 | 0.1 | 10 |
| methyl mercaptan (ppm) | N.D. | N.D. | 4 |

By treating with polyferric sulfate, hydrogen peroxide, and the nitrate, the concentrations of hydrogen sulfide and methyl mercaptan in the dehydrator and the hopper for a dehydrated cake remarkably decreased. When the pretreatment with polyferric sulfate was not conducted, the concentration of hydrogen sulfide in the dehydrator slightly increased while smell in the hopper for a dehydrated cake did not increase in comparison with the case that the pretreatment with polyferric sulfate was conducted.

Example 36

In the same process for treating sludge as that conducted in Example 34, a mixed solution prepared from a 37% by weight solution of iron(III) chloride and nitric acid was added into a manhole 10 at the upper part of the sludge tank 1 in such an amount that the concentration of iron(III) chloride was 665 mg/liter (80 mg/liter as the iron atom) and the concentration of the nitrate ion was 100 mg/liter in the sludge, and hydrogen peroxide B was continuously added into the transfer pipe 3 immediately after the transfer pump 2 which transferred the sludge from the sludge tank 1 in such an amount that the concentration of hydrogen peroxide was 100 mg/liter as 100% hydrogen peroxide. The results of the measurements of hydrogen sulfide and methyl mercaptan in the dehydrator (point of measurement of smell a) are shown in Table 14.

Comparative Example 10

The same treatment as that conducted in Example 36 was conducted except that a 37% by weight solution of iron(III) chloride was added at the manhole 10 at the upper part of the sludge tank 1 in such an amount that the concentration of the iron(III) chloride was 1,258 mg/liter (160 mg/liter as the iron atom) and neither hydrogen peroxide nor nitric acid was added. The results are shown in Table 14.

TABLE 14

|  | Example 36 | Comparative Example 10 |
| --- | --- | --- |
| area around the dehydrator |  |  |
| hydrogen sulfide (ppm) | 3 | 80 |
| methyl mercaptan (ppm) | N.D. | 8 |

As clearly shown in Table 14, the combination of the peroxide and the nitrate ion could enhance the effect of removing smell while the treatment with an iron salt alone was not sufficient for removing smell.

Example 37

Figure 9:
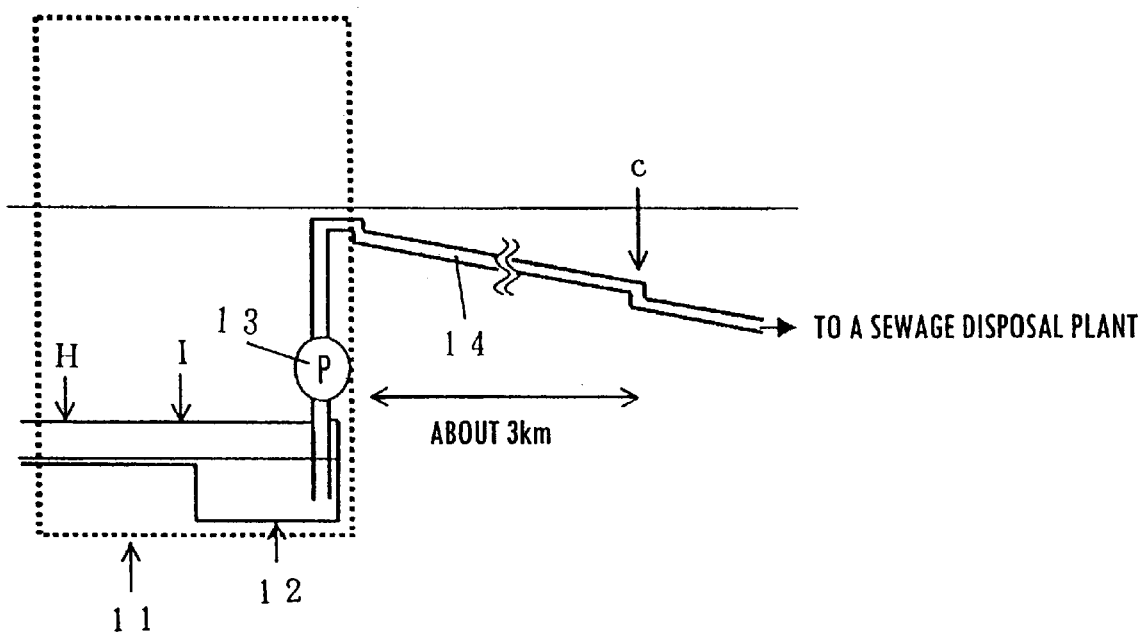
FIG. 9 shows a schematic diagram exhibiting the process for treating sewage conducted in Example 37 and Comparative Example 11.

FIG. 9 shows a schematic diagram exhibiting the process for treating sewage conducted in this Example and in Comparative Example 11 which is described below. Sewage in a pit 12 of a pumping station 11 was transferred to a sewage disposal plant through sewer pipe 14 by a transfer pump 13.

Figure 11:
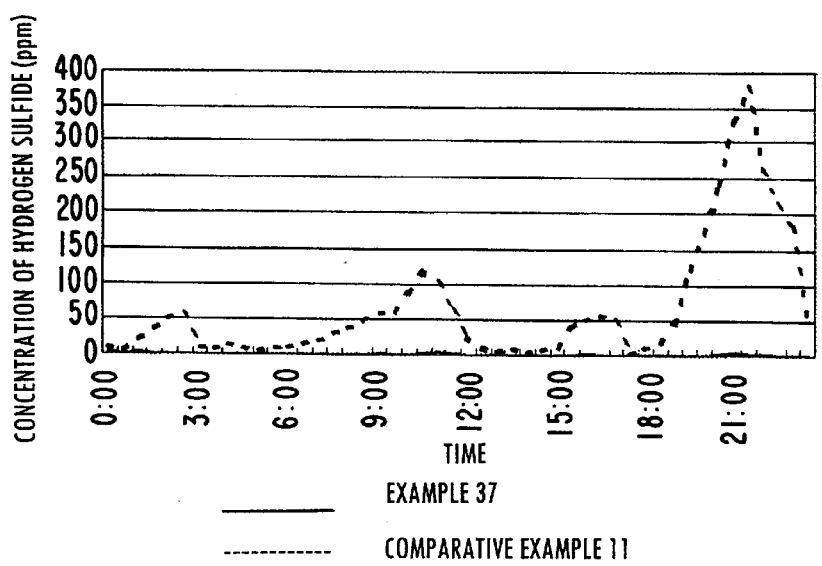
FIG. 11 shows a graph exhibiting the results obtained in Example 37 and Comparative Example 11.

In the above process for treating sewage, a 37% solution of iron(III) chloride H was added into an inlet of a grit chamber of a pumping station 11 in such an amount that the concentration was 39 mg/liter (5 mg/liter as the iron atom) in the sewage, and a mixed solution I containing hydrogen peroxide and nitric acid was continuously added into an outlet of the grit chamber in such an amount that the concentration of hydrogen peroxide was 10 mg/liter as 100% hydrogen peroxide and the concentration of the nitrate ion was 7 mg/liter in the sewage. The result of the measurement of the concentration of hydrogen sulfide in the manhole (point of measurement of smell c) is shown in FIG. 11.

Comparative Example 11

The same treatment as that conducted in Example 37 was conducted except that the deodorant was not added. The result of measurement of the concentration of hydrogen sulfide in the manhole (point of measurement of smell c) is shown in FIG. 11.

By pretreating the sewage with the iron salt and adding the mixed solution of hydrogen peroxide and the nitrate ion, the formation of hydrogen sulfide could be suppressed in the manhole about 3 km downstream of the point of the addition.

Example 38

Figure 10:
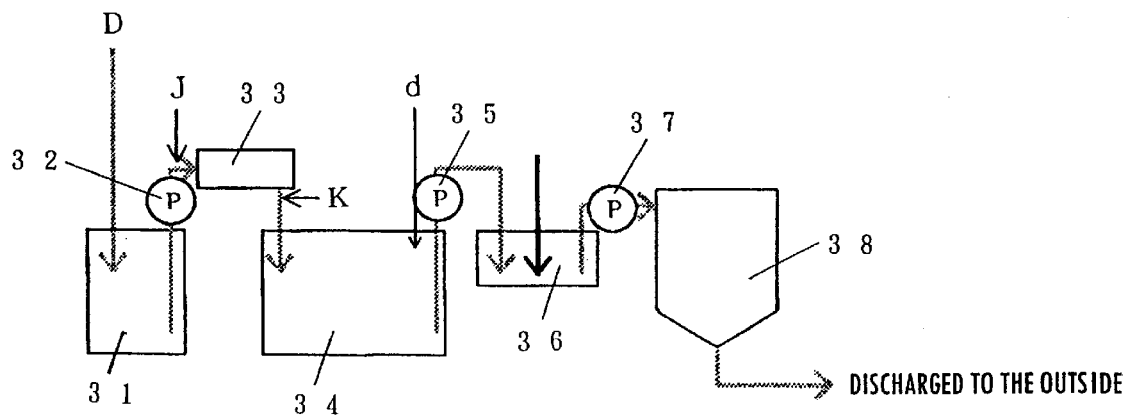
FIG. 10 shows a schematic diagram exhibiting the process for treating waste water conducted in Example 38 and Comparative Example 12.

FIG. 10 shows a schematic diagram exhibiting the process for treating waste water conducted in this Example and in Comparative Example 12 described below. Waste water D which had flowed into a raw water tank 31 was transferred to an adjustment tank 34 through a screen 33 by a pump 32 and then transferred to a mixing tank 36 by a pump 35. After a flocculating agent A was added to the waste water in the mixing tank 36, the waste water was transferred to a floating tank 38 by a pump 37 and then discharged to the outside.

Figure 12:
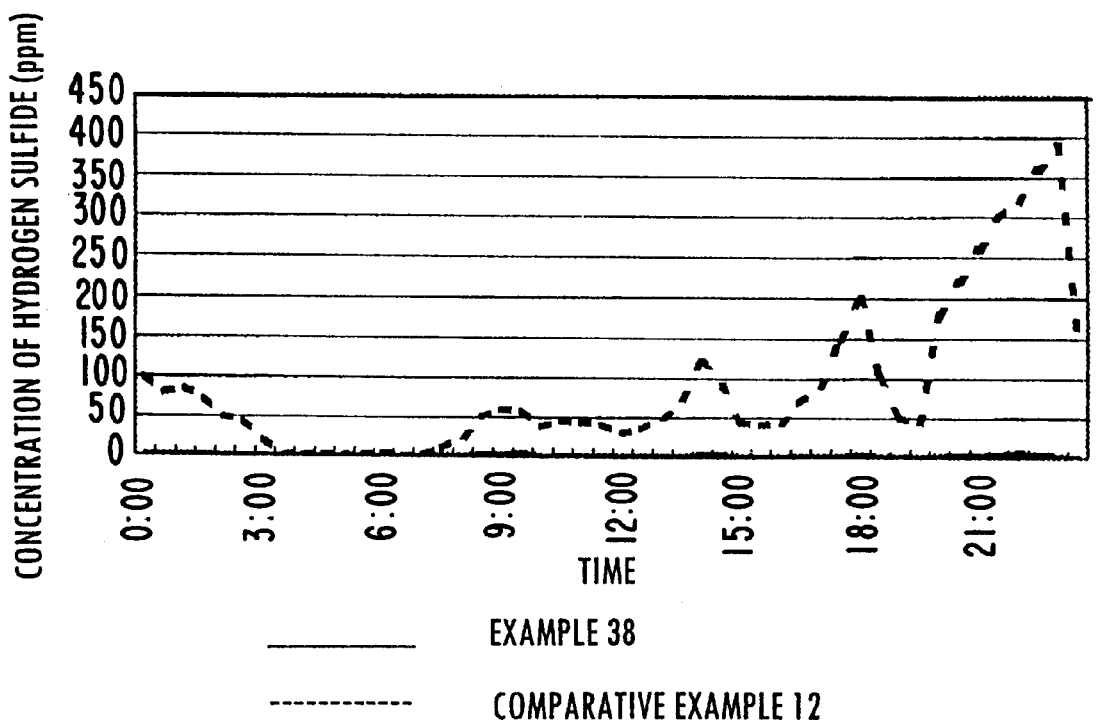
FIG. 12 shows a graph exhibiting the results obtained in Example 38 and Comparative Example 12.

In the above process for treating waste water, a mixed solution J prepared from polyferric sulfate and a 30% by weight aqueous solution of sodium nitrate was added into a pipe immediately after the pump 32 which transferred the waste water D from the raw water tank 31 to the adjustment tank 34 in such an amount that the concentration of the polyferric sulfate was 27 mg/liter (3 mg/liter as the iron atom) and the concentration of the 30% by weight aqueous solution of sodium nitrate was 91 mg/liter (20 mg/liter as the nitrate ion) in the waste water, and a 35% by weight hydrogen peroxide K was continuously added into a pipe after the screen in such an amount that the concentration of hydrogen peroxide was 30 mg/liter as 100% hydrogen peroxide in the waste water. The result of the measurement of the concentration of hydrogen sulfide in the adjustment tank 34 (point of measurement of smell d) is shown in FIG. 12.

Comparative Example 12

The same treatment as that conducted in 38 was conducted except that no deodorant was added. The result of the measurement of the concentration of hydrogen sulfide in the adjustment tank 34 (point of measurement of smell d) is shown in FIG. 12.

By pretreatment with the iron salt and the nitrate ion, followed by addition of hydrogen peroxide, the concentration of hydrogen sulfide in the adjustment tank remarkably decreased, and smell of hydrogen sulfide around the waste water treatment apparatus also remarkably decreased.

What is claimed is:

1. A deodorant for substances containing at least one of hydrogen sulfide and mercaptans which comprises a combination of a peroxide, a chelating agent and a nitrate ion, wherein the chelating agent is included in the deodorant in an amount of 1 to 50,000 ppm by weight of the total amount of the peroxide and the nitrate ion, and wherein the chelating agent is at least one compound selected from the group consisting of ethylenediaminetetraacetic acid, nitrilotriacetic acid, diethylenetriaminepentaacetic acid, triethylenetetraminehexaacetic acid, polyhydroxycarboxylic acids, 1-hydroxyethylidene-1, 1-diphosphonic acid, aminotri-(methylenephosphonic acid), ethylenediaminetetra (methylene-phosphonic acid), diethylenetriaminepenta (methylenephosphonic acid), 1,2-propylenediaminetetra-(methylenephosphonic acid), hexamethylenediaminetetra-(methylenephosphonic acid), triethylenetetraminehexa-(methylenephosphonic acid), triaminotriethylaminehexa-(methylenephosphonic acid), trans-1,2-cyclohexanediaminetetra-(methylenephosphonic acid), glycol ether diaminetetra-(methylenephosphonic acid), and tetraethylenehepta-(methylenephosphonic acid).

2. A deodorant for substances containing at least one of hydrogen sulfide and mercaptans, comprising a combination of hydrogen peroxide, a nitrate ion and a chelating agent, the hydrogen peroxide and the nitrate ion together acting as deodorizing agents for the at least one of hydrogen sulfide and mercaptans, wherein the chelating agent is included in the deodorant in an amount of 1 to 50,000 ppm by weight of the total amount of the hydrogen peroxide and the nitrate ion, and wherein the chelating agent is at least one compound selected from the group consisting of ethylenediaminetetraacetic acid, nitrilotriacetic acid, diethylenetriaminepentaacetic acid, triethylenetetraminehexaacetic acid, polyhydroxycarboxylic acids, 1-hydroxyethylidene-1,1-diphosphonic acid, aminotri-(methylenephosphonic acid), ethylenediaminetetra(methylene-phosphonic acid), diethylenetriaminepenta(methylenephosphonic acid), 1,2-propylenediaminetetra-(methylenephosphonic acid), hexamethylenediaminetetra-(methylenephosphonic acid), triethylenetetraminehexa-(methylenephosphonic acid), triaminotriethylaminehexa-(methylenephosphonic acid), trans-1,2-cyclohexanediaminetetra-(methylenephosphonic acid), glycol ether diaminetetra-(methylenephosphonic acid), and tetraethylenehepta-(methylenephosphonic acid).

3. A deodorant according to claim 2, further comprising a metal salt, with the hydrogen peroxide, the nitrate ion and the metal salt together acting as deodorizing agents for the at least one of hydrogen sulfide and mercaptans.

4. A deodorant according to claim 2, wherein the peroxide is hydrogen peroxide or a salt of percarbonic acid.

5. A deodorant according to claim 2, wherein the nitrate ion is derived from at least one compound selected from the group consisting of nitric, acid, sodium nitrate, potassium nitrate, calcium nitrate, and ammonium nitrate.

6. A deodorant according to claim 3, wherein the peroxide is hydrogen peroxide or a salt of percarbonic acid.

7. A deodorant according to claim 3, wherein the nitrate ion is derived from at least one compound selected from the group consisting of nitric acid, sodium nitrate, potassium nitrate, calcium nitrate, and ammonium nitrate.

8. A deodorant according to claim 3, wherein the metal salt is at least one compound selected from the group consisting of salts of metals belonging to Groups 6 to 12 and 14 of the Periodic Table.

9. A deodorant according to claim 8, wherein the metal salt is at least one compound selected from the group consisting of salts of iron, copper, manganese, zinc, silver, chromium, nickel, cobalt, tin, and lead.

10. A deodorant according to claim 9, wherein the metal salt is an iron salt.

11. A process for deodorization comprising treating a substance for treatment containing at least one compound selected from the group consisting of hydrogen sulfide and mercaptans with a deodorant described in claim 2.

12. A process according to claim 11, wherein the substance for treatment is waste water, sludge, or water discharged from washing apparatuses.

13. A process according to claim 12, wherein the peroxide or the nitrate ion is added into a pipe through which waste water or sludge is transferred.

14. A process for deodorization comprising treating a substance for treatment containing at least one compound selected from the group consisting of hydrogen sulfide and mercaptans with a deodorant described in claim 3.

15. A process according to claim 14, wherein the substance for treatment is waste water, sludge, or water discharged from washing apparatuses.

16. A process according to claim 15, wherein waste water or sludge is treated with an iron salt and subsequently with the peroxide and the nitrate ion.

17. A process according to claim 15, wherein waste water or sludge is treated with an iron salt and the nitrate ion and subsequently with the peroxide.

18. A deodorant according to claim 2, wherein the peroxide is a salt of percarbonic acid.

19. A deodorant according to claim 2, wherein the nitrate ion is derived from at least one compound selected from the group consisting of nitric acid and salts of nitric acid.

20. A process according to claim 11, wherein the peroxide, chelating agent and nitrate ion are mixed together prior to said treating said substance for treatment.

21. A process according to claim 14, wherein the peroxide, chelating agent and nitrate ion are mixed together prior to said treating said substance for treatment.

22. A process according to claim 14, wherein the peroxide, the chelating agent, the nitrate ion and the metal salt are mixed together prior to said treating said substance for treatment.

23. A deodorant according to claim 1, further comprising a metal salt.

24. A deodorant according to claim 3, wherein the metal salt is included in the deodorant in an amount of 0.5 to 300 mg/liter of the substances being treated.

25. A deodorant according to claim 24, wherein the hydrogen peroxide is included in the deodorant in an amount of 2 to 1,000 mg/liter of the substances being treated.

26. A deodorant according to claim 25, wherein the nitrate ion is included in the deodorant in an amount of 2 to 1,000 mg/liter of the substances being treated.

27. A deodorant according to claim 3, wherein the metal salt is included in the deodorant in an amount of 0.1 to 500 mg/liter of the substances being treated.

28. A deodorant according to claim 27, wherein the hydrogen peroxide is included in the deodorant in an amount of 1 to 2,000 mg/liter of the substances being treated.

29. A deodorant according to claim 28, wherein the nitrate ion is included in the deodorant in an amount of 1 to 2,000 mg/liter of the substances being treated.

30. A deodorant according to claim 2, wherein the hydrogen peroxide is included in the deodorant in an amount of 2 to 1,000 mg/liter of the substances being treated.

31. A deodorant according to claim 30, wherein the nitrate ion is included in the deodorant in an amount of 2 to 1,000 mg/liter of the substances being treated.

32. A deodorant according to claim 2, wherein the hydrogen peroxide is included in the deodorant in an amount of 1 to 2,000 mg/liter of the substances being treated.

33. A deodorant according to claim 32, wherein the nitrate ion is included in the deodorant in an amount of 1 to 2,000 mg/liter of the substances being treated.

* * * * *